United States Patent [19]

Horodysky et al.

[11] Patent Number: 4,534,872
[45] Date of Patent: * Aug. 13, 1985

[54] MULTIFUNCTIONAL LUBRICANT ADDITIVES AND COMPOSITIONS THEREOF

[75] Inventors: Andrew G. Horodysky, Cherry Hill; Joan M. Kaminski, Mullica Hill, both of N.J.

[73] Assignee: Mobil Oil Corporation, New York, N.Y.

[ * ] Notice: The portion of the term of this patent subsequent to Jan. 11, 2000 has been disclaimed.

[21] Appl. No.: 519,444

[22] Filed: Aug. 2, 1983

[51] Int. Cl.$^3$ .......................... C10M 1/48; C10M 1/46
[52] U.S. Cl. ............................... 252/32.7 E; 260/399; 556/7; 556/25
[58] Field of Search .................... 252/32.7 E, 32.7 R; 260/429 R, 429.9, 430, 399

[56] References Cited

U.S. PATENT DOCUMENTS

| | | | |
|---|---|---|---|
| 2,921,027 | 1/1960 | Brennan | 252/32.7 E |
| 4,293,430 | 10/1981 | Rivier | 252/32.7 E |
| 4,368,129 | 1/1983 | Horodysky | 252/32.7 E |
| 4,400,283 | 8/1983 | Horodysky et al. | 252/32.7 E |
| 4,410,434 | 10/1983 | Andress | 252/32.7 R |

*Primary Examiner*—John F. Niebling
*Attorney, Agent, or Firm*—Alexander J. McKillop; Michael G. Gilman; Howard M. Flournoy

[57] ABSTRACT

Metal salts of partially borated, partially phosphosulfurized pentaerythritol and trimethyolpropane based hydroxyl-containing esters are effective as multifunctional additives, reducing friction, inhibiting oxidation and reducing bearing corrosion when incorporated into a variety of lubricating media.

22 Claims, No Drawings

4,534,872

MULTIFUNCTIONAL LUBRICANT ADDITIVES AND COMPOSITIONS THEREOF

BACKGROUND OF THE INVENTION

1. Field of the Invention

This invention is directed to multifunctional lubricant additives and to compositions containing same. In a more particular aspect this invention is directed to metal salts of partially borated, partially phosphosulfurized pentaerythritol, dipentaerythritol and trimethylolpropane based hydroxyl-containing esters and to lubricating fluids containing same.

2. Description of Prior Art

The metal surfaces of machinery or engines operating under heavy loads wherein metal slides against metal may undergo excessive wear or corrosion. Often, the lubricants used to protect the metal surfaces deteriorate under such heavy loads and as a result, do not prevent wear at the points of metal to metal contat. Consequently, the performance of the machine or engine will suffer, and in aggravated cases the machine or engine may become completely inoperative.

It is also known that lubricants are prone to oxidative deterioration when subjected to elevated temperatures or even when they are exposed to atmospheric conditions for long periods of time. Such deterioration of lubricants, including lubricating oils and greases, produces loss of lubricating properties of the oil, grease or other lubricant subjected to oxidation.

Accordingly, there is a need for a multifunctional additive system capable of effectively reducing wear, inhibiting corrosion and reducing oxidative deterioration. There have been many attempts to device additive systems which would provide satisfactory protection in imparting friction reducing, antioxidant and anticorrosion properties to lubricants. Many prior art additives have, however, been only marginally effective in accomplishing such objective except at unacceptably high concentrations, especially when the lubricants are subjected to drastic oxidizing conditions.

U.S. Pat. No. 3,652,410 describes multifunctional lubricant additive compositions comprising overbased metal salts and sulfur-containing compounds. U.S. Pat. No. 4,162,224 describes antiwear and antioxidant additive compounds comprising certain borates of bisoxazolines. However, no known art discloses or suggests the use of metal salts of partially borated, partially phosphosulfurized pentaerythritol or trimethylolpropane based hydroxyl-containing esters as multifunctional lubricant additives.

SUMMARY OF THE INVENTION

In accordance with the present invention, it has been found that certain novel metal salts of partially borated, partially phosphosulfurized pentaerythritol and trimethylolpropane based hydroxyl-containing esters reduce friction when incorporated into lubricating fluids. These novel additives thereby reduce engine wear, inhibit oxidation and concomitantly inhibit bearing corrosion when used in, for example, internal conbustion engine lubricants.

The novel compounds of this invention are metal salts of partially borated, partially phosphosulfurized pentaerythritol and metal salts of partially borated, partially phosphosulfurized trimethylolalkane based hydroxyl-containing esters. Zinc is the preferred metal although other metals such as nickel, iron, cobalt and molybdenum are highly useful. Lubricant compositions containing same are substantially improved with respect to antioxidant, antiwear and anticorrosion properties as well as reducing friction.

DESCRIPTION OF PREFERRED EMBODIMENTS

The novel compounds of this invention can be prepared by first partially phosphosulfurizing a pentaerythritol or a trimethylolalkane based hydroxyl-containing ester by (1) reacting the hydroxyl-containing ester with a phosphosulfur compound such as phosphorus pentasulfide and (2) then reacting the partially phosphosulfurized compound, for example, partially phosphosulfurized dipentaerythritol dioleate with a metal compound such as zinc oxide and (3) thereafter borating the metal salt of the partially phosphosulfurized pentaerythritol and trimethylolalkane based hydroxyl-containing ester in any convenient manner.

The novel additives of this invention can also be prepared by first partially phosphosulfurizing a hydroxyl-containing ester with a phosphorus sulfide, (2) then partially reacting the intermediate with a boron containing compound such as boric acid or low molecular weight trialkyl borate, and (3) then reacting the partially phosphosulfurized, partially borated compound with a metal compound such as zinc oxide. Another possible method of synthesizing the novel additives of this invention includes (1) partially reacting the hydroxyl-containing ester with a boron containing compound, (2) then partially phosphosulfurizing the intermediate, and (3) then finally reacting it with a metal compound. Other methods known in the art can also be used to form the metal salts of these partially borated, partially phosphosulfurized hydroxyl-containing esters. Mixtures of hydroxyl-containing esters can also be used. Partially is meant to include less than molar or less than equivalent quantities.

Reaction of, such as $P_2S_5$, a suitable phosphorus compound with the hydroxyl group can take place at 50° C. to about 125° C., preferably at 60° C. to about 90° C. A solvent can be used if desired.

In the phosphosulfurization 5 to 95% of the available hydroxyl groups may react with the phosphorus polysulfide. Preferably, 25-75% of the available hydroxyl groups are phosphosulfurized.

Reaction with a suitable metal compound to form the metal salt can take place at 50° C. to about 125° C., preferably from about 60° C. to about 90° C. A solvent is often desirable. The metal compound can include metal oxide, hydroxide, chloride, bromide, carbonate, etc. e.g., zinc oxide or zinc hydroxide, or nickel, silver, or cadmium salts.

The metal salts of the partially phosphosulfurized compounds may be reacted directly with boric acid or a suitable boron compound including for example, trialkyl borates such as trimethyl borate, triethyl borate or tributyl borate. Reaction is usually effected at a temperature between about 70° C. and about 150° C. employing a molar ratio of the partially phosphosulfurized compound to the boric acid or other boron compound of between about 1:5 to 10:1. At least 5% and up to 95% or more of the available hydroxyl groups should be reacted with the boronating species. Preferred mole ratios are from about 1:3 to 3:1.

The hydroxyl-containing esters used in preparing the additive compounds of this invention may be obtained commercially or prepared in any convenient manner known to the art. Specific members include pentaerythritol, dipentaerythritol, or trimethylolalkanes such as trimethylolpropane and the like.

The synthetic ester fluids are made by an acid/alcohol reaction selected and selectively reacted so that the product of the reaction will contain at least one free hydroxyl group (not connected with a carboxyl group). The free hydroxyl group subsequently used for phosphosulfurization will then be derived from the polyhydric alcohol. Those can be made by reacting the acid and alcohol at elevated temperatures up to 260° C. or more, in the presence of a catalyst such as p-toluenesulforic acid. A solvent such as toluene or xylene can be used.

The acids useful as reactants with these alcohols include any monocarboxylic acid of the formula

R—COOH where R is a straight chain, branched chain or cyclic hydrocarbyl group, or alkenyl, cycloalkyl or arylalkyl or alkylaryl group containing from about 4 to about 30 carbon atoms, or mixtures thereof, but not containing an alcoholic hydroxyl group. A particularly effective acid or mixture of acids are those having from 5 to 31 carbon atoms. Some of the acids that are suitable are valeric hexanoic (caproic), heptanoic, octanoic, nonanoic (pelargonic), ecanoic (capric), pivalic, myristic, lauric, oleic, stearic, and isostearic acids and the like and mixtures thereof. The acids are reacted with polyols or polyhydric alcohols having the general formula $RC[(CH_2)_xOH]_y$ or
$[HO(CH_2)_x]_3C(CH_2)_xO(CH_2)_xC[(CH_2)_xOH]_3$ where R may be hydrogen of hydrocarbyl of from about 1 to 8 carbon atoms, x is an integer from about 1 to about 4, and y is from about 3 to about 4, R can also be $[(CH_2)_xOH]$.

Typical polyhydric alcohols contemplated for use herein include those containing from about 6 to 30 carbon atoms and from about 3 to 4 hydroxyl groups.

Among the esters particularly contemplated for use herein are mono and diesters of trimethylolpropane and the mono and diesters of pentaerythritol such as pentaerythritol dioleate, trimethylolpropane monooleate, trimethylolpropane monostearate, pentaerythritol monostearate, pentaerythritol monooleate monostearate, pentaerythritol distearate, and pentaerythritol isostearate. Preferably the hydroxyl-containing esters are those where one to two hydroxyl groups are available for phosphosulfurization and two ester groups are found in the molecule. This may be accomplished by reacting the trihydric alcohols with one mole of carboxylic acid and tetrahydric alcohols with from 1 to 2 moles of carboxylic acid. The sum total of available hydroxyl groups and ester linkages must equal at least three in the reactive hydroxyl-containing esters.

Specific examples of suitable hydroxyester include pentaerythritol mono, di- and small amounts of trioleic esters, the dipentaerythritol esters, the mono and diesters wherein the acids are selected from mixed $C_5$ to $C_{18}$ acids, e.g. mixtures of pelargonic and oleic acids such as pentaerythritol monopelargonate monooleic. Included are the mono and diesters of trimethylolalkanes (e.g., trimethylolpropane) such as trimethylolpropane monooleate and trimethylolpropane monovalerate; small amounts of diesters of a trimethylolalkane can also be present. Preferably the trimethylolpropanes are monoesters. Mixtures of mono and diesters of polyhydric acids can also be used.

The above-described partially borated, partially phosphosulfurized hydroxyl-containing esters may be incorporated into any suitable lubricating media which comprise oils of lubricating viscosity, e.g., mineral or synthetic; or mixtures of mineral and synthetic or greases in which the aforementioned oils are employed as a vehicle or into such functional fluids as hydraulic fluids, brake fluids, power transmission fluids and the like. In general, mineral oils, employed as the lubricant oil, or grease vehicle may be of any suitable lubricating viscosity range, as for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation. The fully formulated lubricating oils may include a variety of additives (for their known purpose) such as dispersants, detergents, inhibitors, antiwear agents, antioxidant, antifoam, pour depressant and other additives including phenates, sulfonates and zinc dithiophosphates.

In instances where synthetic oil, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl)sebacate, di(2-ethylhexyl)adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl)ether, phenoxy phenylethers, etc.

As hereinbefore indicated, the aforementioned additive compounds may be incorporated as multifunctional agents in grease compositions. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above-described additives, are combined with a grease-forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickners, such as surface-modified clays and silicas, aryl ureas, calcium complexes and similar materials. In general, grease thickners may be employed which do not melt and dissolve when used at the required temperature within a particular environment; soap thickens such as metallic (lithium or calcium) soaps including hydroxy stearate and/or stearate soaps can be used however, in all other respects, any material which is normally employed for thickening or gelling hydrocarbon fluids or forming greases can be used in preparing the aforementioned improved greases in accordance with the present invention.

The hydroxyesters of this invention contain both boron and phosphorus linkages, thereby, combining the advantages provided by both these moieties in one composition which has far superior characteristics than those provided by mere mixtures of individual borated and phosphosulfurized hydroxyl-containing esters. We do not wish to be held to a particular theory but we believe that the boron in the partially borated partially phosphosulfurized hydroxyl-containing hydrocarbyl ester provides the enhanced friction-reduction and antioxidation and that the phosphorus-sulfur-metal salt moiety provides antiwear/extreme pressure, antioxidation and bearing corrosion inhibiting characteristics. In any event the data disclosed herein clearly shows the multifunctional and synergistic contribution of the various elements of the metal salts of partially borated, partially phosphosulfurized hydroxyl-containing esters in accordance with the present invention.

It is also noted that the novel additives in accordance with this invention may be used to advantage in conjunction with any known lubricant additive system.

DESCRIPTION OF SPECIFIC EMBODIMENTS

EXAMPLE 1

Pentaerythritol Based Hydroxyl-Containing Ester

This example illustrates the synthesis of a hydroxyl-containing ester. One mole of pentaerythritol, one and one-half moles of oleic acid and one-half moles of pelargonic acid were heated in the present of a catalytic amount of p-toluene sulfonic acid (i.e., 0.1% of the combined weight of reactants) at a temperature of up to 240° C. Water was simultaneously removed and the reaction was continued until an acid number of less than 1 was obtained. The partial ester was filtered to yield a clear amber fluid containing 2 free hydroxyl groups.

EXAMPLE 2

Zinc Salt of Partially Phosphosulfurized Pentaerythritol Based Hydroxyl-Containing Ester Approximately 420 grams of a pentaerythritol based hydroxyl-containing ester prepared as described in Example 1 were charged to a reactor equipped with a stirrer, thermometer, condenser and a caustic scrubber. Approximately 420 grams of a hydrocarbon diluent process oil were added along with 30 grams benzene solvent. The mixture was heated to 70°–80° C. and 39 grams of phosphorus pentasulfide were added over a period of 1 hour. The reaction mixture was further held at 90° C. for 4 additional hours at which point $H_2O$ evolution diminished. The benzene solvent was removed by vacuum distillation and the partially phosphosulfurized hydroxyl-containing ester was filtered hot over paper to yield a clear amber liquid containing:
  1.2% phosphorus
  2.3% sulfur Approximately 240 grams of the above partially phosphosulfurized ester was reacted with 16 grams zinc oxide in the presence of 30 grams benzene and 3 grams 2-propanol solvents for 4 hours @85°–95° C. The solvents were removed by vacuum distillation to 100° C. The product was filtered over diatomaceous earth to yield a clear amber fluid.

EXAMPLE 3

Partially Borated Zinc Salt of Partially Phosphosulfurized Pentaerythritol Based Hydroxyl-Containing Ester Approximately 85 grams of the zinc salt of partially phosphosulfurized pentaerythritol based hydroxyl-containing ester was prepared as described in Example 2 were charged to a stirred reactor with 60 ml toluene solvent and 2.7 grams boric acid. The reactor was equipped with a Dean-Stark trap to collect water produced during the reaction. The reactants were heated up to 160° C. during a 5 hour period until water evolution terminated. The solvent was removed by vacuum distillation up to 150° C. and the borated product was filtered through diatomaceous earth to yield a clear amber fluid.

EXAMPLE 4

Trimethylolpropane Based Hydroxyl-Containing Ester

This example illustrates the synthesis of a hydroxyl-containing ester. One mole of trimethylolpropane, one mole of oleic acid and one-half mole of pelargonic acid were heated in the presence of a catalytic amount of p-toluene sulfonic acid at a temperature of up to 240° C. Water was simultaneously removed and the reaction was continued until an acid number of less than 1 was obtained. The partial ester was filtered to yield a clear amber fluid.

EXAMPLE 5

Zinc Salt of Partially Phosphosulfurized Trimethylolpropane Based Hydroxyl-Containing Ester Approximately 271 grams of a trimethylolpropane based hydroxyl-containing ester was prepared as described in Example 4 were charged to a reactor equipped with a stirrer, thermometer, condenser and a caustic scrubber. Aproximately 271 grams of a hydrocarbon diluent process oil was added along with 30 grams benzene solvent. The mixture was heated to 80° C. and 27 grams phosphorus pentasulfide was added over a period of one hour. The benzene solvent was removed by vacuum distillation and the partially phosphosulfurized hydroxyl-containing ester was filtered hot through paper to yield a clear amber fluid containing:
  1.0% phosphorus
  2.0% sulfur Approximately 200 grams of the above partially phosphosulfurized ester were reacted with 12 grams zinc oxide in the presence of 30 grams benzene and 3 grams 2-propanol solvents for 4 hours as 85°–95° C. The solvents were removed by vacuum distillation and the product was filtered over diatomaceous earth to yield a clear amber fluid.

EXAMPLE 6

Partially Borated Zinc Salt of Partially Phosphosulfurized Trimethylolpropane Based Hydroxyl-Containing Ester Approximately 85 grams of the zinc salt of partially phosphosulfurized trimethylolpropane based hydroxyl-containing ester prepared as described in Example 5 was charged to a stirred reactor equiped with a Dean- Stark trap. Approximately 2¼ grams boric acid was added along with 50 ml toluene solvent. The reactants were heated up to 155° C. during a 4½ hour period until water evolution was no longer visible in the Dean-Stark trap. The solvent was removed by vacuum distillation and the borated product was filtered over diatomaceous earth to yield a clear amber fluid.

EXAMPLE 7

Partially Borated Zinc Salt of Partially Phsophosulfurized Pentaerythritol Based Hydroxyl-Containing Ester Approximately 200 g of partially phosphosulfurized pentaaeythritol based hydroxyl-containing ester proposed as described in the first portion of Example 2 was charged to a stirred glass reactor with 150 g of diluent hydrocarbon oil, 12 g boric acid and 50 g toluene solvent. The mixture was refluxed at up to 140° C. until no more water evolved. A nitrogen purge was used during this reaction. The toluene solvent was removed by vacuum distillation and then the batch was filtered hot through paper.

Aproximately 227 g of this filtrate, 15 g zinc oxide and 45 g 2-propanol solvent was refluxed for 5 hours at about 90° C. The solvent was removed by vacuum distillation and the product was filtered through paper. The product was a viscous liquid.

Some of the metal salts of the partially borated, partially phosphosulfurized hydroxyl containing esters were blended into a fully formulated automotive engine oil (SAE 5W-20) containing detergent/dispersant/inhibitor package and tested on the Low Velocity Friction Apparatus (LVFA). Results are reported in Table 1. Friction was significantly reduced relative to the base oil or the unborated phosphosulfurized salts. Reductions of up to 48% in the coefficient of friction were measured. Furthermore, all of the additives also had good copper corrosion inhibition. All of the copper strip corrosion test results except one were 1A or 1B, see Table 3.

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces were submerged in the test lubricant. Friction between the steel surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infintely variable-speed hydraulic transmission driven by a ½ HP electric motor. To vary the sliding speed, the output speed of the transmission is regulated by a lever cam-motor arrangement.

Procedure

The rubbing surfaces and 12-13 ml. of test lubricant are place on the LVFA. A 500 psi load is applied, and the sliding speed is maintained at 40 fpm at ambient temperature for a few minutes. A plot of coefficients of friction ($U_k$) over a range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 6 to 8 microinches. The percentages by weight are percentages by weight of the total lubricating oil composition, including the usual additive package. The data are percent decrease in friction according to:

$$\frac{(U_k \text{ of oil alone}) - (U_k \text{ of Additive plus oil})}{(U_k \text{ of oil alone})} \times 100$$

Thus, the corresponding value for the oil alone would be zero for the form of the data used in Table 1 below.

TABLE 1

Friction Characteristics

| Example No. | Additive Conc., Wt. % | Reduction or % Change in Coefficient of Friction | |
|---|---|---|---|
| | | 5 Ft./Min. | 30 Ft./Min. |
| Base Oil | — | 0 | 0 |
| Example 2 | | | |
| Zinc salt of partially phosphosulfurized pentaerythritol based hydroxyl-containing ester | 2 | 8 | 8 |
| | 4 | 14 | 15 |
| Example 3 | | | |
| Partially borated zinc salt of partially phosphosulfurized pentaerythritol based hydroxyl-containing ester | 3 | 23 | 13 |
| Example 5 | | | |
| Zinc salt of partially phosphosulfurized trimethylolpropane based hydroxyl-containing ester | 4 | 7 | 8 |
| Example 6 | | | |
| Partially borated zinc salt of partially phosphosulfurized trimethylolpropane based hydroxyl-containing ester | 3 | 34 | 26 |
| Example 7 | | | |
| Zinc salt of partially phosphosulfurized and partially borated pentaerythritol based hydroxyl-containing ester. | 4 | 21 | 22 |

Certain of the examples were also tested for their antioxidation characteristics in the B-10 Catalytic Oxidation Test at 325° F. for 40 hours. The test lubricant composition is subjected to a stream of air which is bubbled through the composition at a rate of 5 liters per hour at 325° F. for 40 hours. Present in the composition comprising a 200 seconds paraffinic netural oil in addition to the additive compound were metals commonly used as materials to construct engines namely:

(a) 15.6 sq. in. of sand-blasted iron wire;
(b) 0.78 sq. in. of polished copper wire;
(c) 0.87 sq. in. of polished aluminum wire; and
(d) 0.107 sq. in. of polished lead surface.

The test results are reported below in Table 2.

TABLE 2

Catalytic Oxidation Test 40 Hours @ 325° F.

| | Additive Conc., Wt. % | Lead Loss, Mg | % Increase in Visc. of Oxidized Oil Using KV @ 210° F. | Neut. Number NN |
|---|---|---|---|---|
| Base Oil, 0% Additive 200" Solvent Paraffinic Neutral Lubricating Oil | — | 1.2 | 67 | 3.62 |
| Example 2 Zinc salt of partially phosphosulfurized pentaerythritol based hydroxyl-containing ester | 1 3 | 0.0 0.5 | 4 7 | 1.36 0.96 |
| Example 5 Zinc salt of partially phosphosulfurized trimethylolpropane based hydroxyl-containing ester | 1 3 | 0.0 0.0 | 8 5 | — 1.80 |
| Example 7 Zinc salt of partially phosphosulfurized and partially borated pentaerythritol-based hydroxyl-containing ester | 1 3 | 0.0 0.0 | 7 4 | 1.89 1.38 |

Copper corrosion inhibiting properties of the exemplary compounds were tested via copper corrosivity tests, ASTM D 130-6, ASTM D 130-9. The results are reported in Table 3 below.

TABLE 3

Copper Strip Corrosivity Characteristics

| Example No. | Concentration in 200° SPN* Lubricating Oil | ASTM D130-6 250° F., 3 Hrs. | ASTM D130-9 210° F., 6 Hrs |
|---|---|---|---|
| Example 2 Zinc salt of partially phosphosulfurized pentaerythritol based hydroxyl-containing ester | 1 3 | 1B 1B | 1B 1B |
| Example 5 Zinc salt of partially phosphosulfurized trimethylolpropane based hydroxyl-containing ester | 1 3 | 1B — | 1A 1B |
| Example 6 Partially borated zinc salt of partially phosphosulfurized trimethylolpropane based hydroxyl-containing ester | 1 3 | 2A 1B | 1B 1B |
| Example 7 Zinc salt partially phosphosulfurized and partially borated pentaerythritol-containing ester | 1 3 | 1A 1A | 1A 1A |

*SPN = solvent paraffinic neutral lubricating oil.

We claim:

1. A lubricant composition comprising a major proportion of an oil of lubricating viscosity or grease or other solid lubricant prepared therefrom and a minor effective amount of a multifunctional additive consisting of a metal salt of a partially borated, partially phosphosulfurized hydroxyl-containing ester derived from polyols selected from pentaerythritol, dipentaerythritol, substituted pentaerythritol or mixtures thereof and trimethylolalkanes or mixtures of trimethylolalkanes.

2. The composition of claim 1 wherein prior to phosphosulfurization said hydroxyl-containing esters contain from 1 to 3 hydroxyl groups available for said phosphosulfurization and contain at least one ester group therein with the proviso that the sum total of available hydroxyl groups and ester linkages must be at least 3.

3. The composition of claim 1 wherein the hydroxyl-containing esters are selected from the group consisting of mono and diesters of trimethylolpropane and mono and diesters of pentaerythritol.

4. The composition of claim 1 wherein the metal salts are derived from the group consisting of metal oxides, metal hydroxides, metal chlorides, metal bromides and metal carbonates.

5. The composition of claim 1 wherein the metal salt is derived from a zinc compound.

6. The composition of claim 5 wherein the zinc compound is zinc oxide or zinc hydroxide.

7. The composition of claim 6 wherein the zinc compound is zinc oxide.

8. The composition of claim 7 wherein the additive compound is a partially borated zinc salt of a partially phosphosulfurized pentaaerythritol based hydroxyl-containing ester.

9. The composition of claim 7 wherein the additive compound is a partially borated zinc salt of a partially phosphosulfurized trimethylolpropane based hydroxyl-containing ester.

10. The composition of claim 1 wherein the oil of lubricating viscosity is selected from mineral oils or fractions thereof, and synthetic oils, or mixtures of mineral and synthetic oils.

11. The composition of claim 1 wherein said oil is a mineral oil.

12. The composition of claim 1 wherein said oil is a synthetic oil.

13. The composition of claim 1 wherein said major proportion is a grease.

14. A metal salt of a borated, partially phosphosulfurized hydroxyl-containing ester derived from a synthetic ester fluid prepared by an acid alcohol reaction wherein said acid is a monocarboxylic acid of the formula $$R-COOH$$

where R is a straight chain, branched or cyclic hydrocarbyl group including alkyl, alkenyl, arylalkyl, or alkylaryl group containing from about 4 to about 30 carbon atoms or mixtures thereof with the proviso that said acid does not contain an alcoholic hydroxy group and wherein said alcohol is a polyol having the general formula $$RC[(CH_2)_xOH]_y \text{ or}$$
$$[HO(CH_2)_x]_3C(CH_2)_xO(CH_2)_xC[(CH_2)_xOH]_3$$

where R may be hydrogen or hydrocarbyl of from about 1 to 8 carbon atoms, x is an integer from about 1 to about 4, and y is an integer of from about 3 to about 4, R can also be [(CH_2)_xOH].

15. The compound of claim 14 wherein the metal component of said metal salt is derived from compounds selected from the group consisting of metal oxides, metal hydroxides, metal chlorides, metal bromides and metal carbonates.

16. The compound of claim 14 wherein the metal compound is selected from a zinc compound.

17. The compound of claim 16 wherein the zinc compound is a zinc oxide or zinc hydroxide.

18. The compound of claim 14 wherein the borated, partially phosphosulfurized hydroxyl-containing ester is a partially borated zinc salt of partially phosphosulfurized pentaerythritol based hydroxyl-containing ester.

19. The compound of claim 14 wherein the borated, partially phosphosulfurized hydroxyl-containing ester is a partially borated zinc salt of a partially phosphosulfurized trimethylolpropane based hydroxyl-containing ester.

20. The compound of claim 18 wherein the hydroxyl-containing ester moiety is based on a mixture of oleic and pelargonic acids.

21. The compound of claim 19 wherein the hydroxyl-containing ester moiety is based on a mixture of oleic and pelargonic acids.

22. A method of reducing fuel consumption in an internal combustion engine comprising treating the moving surface thereof with a lubricant composition as described in claims 1 or 2.

* * * * *